US 7,799,063 B2

(12) United States Patent
Ingram et al.

(10) Patent No.: US 7,799,063 B2
(45) Date of Patent: Sep. 21, 2010

(54) THERAPEUTIC HOT/COLD PAD (75) Inventors: Aaron Neil Ingram, Canton, GA (US);
Mark Herman Bruder, Alpharetta, GA (US)

(73) Assignee: Bruder Healthcare Company, Alpharetta, GA (US)

( * ) Notice: Subject to any disclaimer, the term of this patent is extended or adjusted under 35 U.S.C. 154(b) by 1740 days.

(21) Appl. No.: 10/423,198

(22) Filed: Apr. 25, 2003

(65) Prior Publication Data
US 2003/0204227 A1    Oct. 30, 2003

Related U.S. Application Data

(60) Provisional application No. 60/375,886, filed on Apr. 25, 2002.

(51) Int. Cl.
*A61F 7/00* (2006.01)
(52) U.S. Cl. .................. 607/104; 607/108; 607/109; 607/110; 607/111; 607/114
(58) Field of Classification Search .............. 607/96, 607/108–112, 114; 62/530; 5/655.5
See application file for complete search history.

(56) References Cited

U.S. PATENT DOCUMENTS

| 3,574,873 | A | * | 4/1971 | Weinstein | 5/655.5 |
|---|---|---|---|---|---|
| 4,981,135 | A | * | 1/1991 | Hardy | 607/108 |
| 6,132,455 | A | * | 10/2000 | Shang | 607/108 |
| 6,700,032 | B1 | * | 3/2004 | Gray | 602/48 |
| 2002/0103520 | A1 | * | 8/2002 | Latham | 607/108 |
| 2003/0097164 | A1 | * | 5/2003 | Stapf et al. | 607/114 |

* cited by examiner

*Primary Examiner*—Roy D Gibson
(74) *Attorney, Agent, or Firm*—Gardner Groff Greenwald & Villanueva, PC (57) ABSTRACT

The invention provides an improved hot/cold therapy pad consisting of a thermally conductive fluid and a discrete matrix insert contained within an outer envelope. The matrix insert has significant void space (over 50%) and is chemically inert relative to the other components within the envelope. The matrix has low bulk density and may be formed by bonding fibers together to form a mat. This matrix serves to reduce the flow of the thermally conductive fluid and provide for more effective and consistent heat (cold) transfer from the pad to the skin. The thermally conductive fluid has a viscosity greater than water and is stable over the typical range of hot/cold therapy applications. The invention eliminates saddle-bagging in hot and cold therapy applications.

27 Claims, 11 Drawing Sheets

Cutaway Section of Typical Construction of Design

3A Exterior Seams/Seal

3B Surface Materials

3C Discrete Matrix

3D Interior Filled with thermal media

Figure 1: Diagram showing a typical construction of design

1A Multiple channels shown.

1B Seams may be formed by RF, Ultrasonic, Sewing, Gluing, Heat Sealing, etc. or any combination of above.

1C Surface may be single layered material, laminate, or multilayered construction.

1D Cutaway version showing internal matrix

Figure 2: Multicelled construction showing cutaway of matrix as solid sheet across entire product.

Figure 3: Cutaway Section of Typical Construction of Design

3A Exterior Seams/Seal

3B Surface Materials

3C Discrete Matrix

3D Interior Filled with thermal media

Figure 4: One method of staking the matrix into a fixed position within the pad

4A Exterior Seam/Seal

4B Staking may be by RF, Ultrasonic, Gluing, Heat Sealing, Laminating, etc.

4C Various sizes and configurations of the stake may be used

4D Discrete Matrix Unit Shown

4E Thermal Media Fill, cutaway shown.

Figure 5: One Alternative method of fixing the matrix position

Figure 6

Prototype matrix inside clear bag. Shows the discrete matrix unit, one type of thermal media.

Figure 7

Prototype matrix inside clear bag. Shows the discrete matrix unit, another type of thermal media.

Figure 8

Example of discrete matrix unit contained in individual channels before addition of the thermal media and before sealing.

8A Individual channels

8B Individual Matrix units

Figure 9

Single matrix inserted within a body and then multiple channels formed across the surface. Cut away shown.

9A Channels

9B Single Matrix Sheet

Figure 10
Matrix having non-uniform thickness across its body.

Figure 11
Matrix having pre-formed shape in three dimensions.

THERAPEUTIC HOT/COLD PAD

CROSS REFERENCE TO RELATED APPLICATIONS

This application claims priority to, and the benefit of the filing date of U.S. patent application No. 60/375,886, filed on Apr. 25, 2002, in the United States Patent and Trademark Office.

FIELD OF THE INVENTION

The present invention relates in general to application of a wide range of therapeutic modalities (heat therapy, cold therapy, contrast therapy). More particularly, the present invention relates to a hot/cold pad used to deliver these therapies.

BACKGROUND OF THE INVENTION

Application of heat therapy, cold therapy (cryotherapy), and contrast therapy (alternating heat and cold therapy) is used to treat a multitude of conditions including muscle and joint pain, strains, sprains, a variety of arthritic conditions, menstrual cramps, and a variety of other maladies. The earliest applications of heat therapy used hot towels or hot stones wrapped in towels. Electric heating pads, clay filled packs kept in hot water tanks, gel packs, alumina and grain packs heated in the microwaves, hot water bottles, water recirculation systems, and paraffin baths have been the methods available to application of heat therapy.

Application of cold therapy has been done using ice bags, gel packs, and water recirculation systems. In each of the methods of application, a heat or cold pack is directly applied to the body for the treatment time of typically 20 to 30 minutes. In some cases, ties or elastic straps have been provided to affix the treatment pack to the body, but in many cases the pack simply rests on the targeted area.

Commercially available hot and cold packs use various thermally conductive solutions and suspensions to provide heat (cold) transfer in hot and cold therapy packs. All of these products use water, glycols, glycerin, or other organic liquids as one of their principal components. They utilize a variety of thickening agents that are designed to increase the viscosity of the fluid and reduce its naturally occurring free flowing characteristics.

A significant shortcoming of currently available technologies is that they do not provide for consistent delivery of hot or cold therapy. Most commonly used hot and cold packs use some form of liquid or gel as the medium that stores heat or cold to be transferred to the body on application. Because the liquid/gel is free flowing within the containing envelope, there is an uneven distribution of the liquid/gel within the pack and saddle-bagging in the region of application is a common complaint. This saddle-bagging results in uneven distribution of heat (or cold) and a less than optimum outcome of the modality. This is specially true for application to body parts of small cross-section (fingers, wrists, etc.), application to children, and veterinary applications to small animals. Addition of thickening and gelling agents is not sufficient to overcome this limitation. Excessive amounts of gelling/thickening agents into the mixture result in a semi-solid hot/cold pack that may become brittle and fracture when cold. The contents may break into smaller, non-uniform pieces which remain discrete and do not return to a single mass. Furthermore, increasing the gel viscosity can be costly and ineffective.

Addition of traditional low density open cell or closed cell (sponge) foams does not address the poor performance of existing hot/cold packs either. Use of closed cell is not effective because the liquid/gel formulations cannot occupy the void spaces present in the foam. Its use gives the impression of mass and improved liquid/gel distribution, but in no way reduces the saddle-bagging because the material voids are isolated from the liquid or gel. The liquid still saddle-bags and the foam only gives the illusion of benefit.

Use of open cell foams (sponge) necessitates selection of low viscosity fluids (water, etc) that can readily flow into the open cells. High viscosity formulations cannot enter the voids. In the low viscosity version, fluids flow into and out of the through the cells and pool outside the foam. Presence of the foam again creates the illusion of benefit, does not restrict the flow of the liquid. Efforts to utilize more viscous gels and open celled foams have not been satisfactory because air becomes trapped within the pack resulting in significant loss of efficacy. Because the thicker gels cannot penetrate into the void space easily, saddle-bagging continues to be manifested during application. Once other side effect is that the air can later release into the bag resulting in pillowing of the gel packs. This pillowing is further detrimental to the optimum application of heat or cold.

Optimum heat transfer (or cold transfer) occurs when there is good physical contact between the hot/cold pack and the skin. Additionally, uniform heat transfer is made possible by both good physical contact between the surfaces and uniform distribution of the liquid/gel in the cold pack, even when applied to small limbs and in a vertical orientation. It is the vertical orientation, coupled with low viscosity fluids and ineffective designs that amplifies the undesirable saddle-bagging.

SUMMARY OF THE INVENTION

The invention is an improved thermal therapy pad that incorporates a self-contained, discrete, matrix structure and a thermally conductive fluid (media) contained in a surrounding envelope. The matrix structure reduces the apparent fluidity of the thermal media without chemically or physically bonding to it. The matrix acts to restrict free flow of the fluid and increase the apparent viscosity of the fluid. Additionally, the matrix contains significant accessible void space to allow extremely viscous fluids to enter without entrapment of air. The resulting invention is an improved hot/cold pad designed for the application of a broad range of therapeutic modalities. The invention is applicable for both human and animal therapeutic modalities, as well as commercial applications where hot and cold media are required (shipping temperature sensitive products, short term preservation and stability of biological agents and drugs, etc.)

DETAILED DESCRIPTION OF THE DRAWINGS

Figure 1:
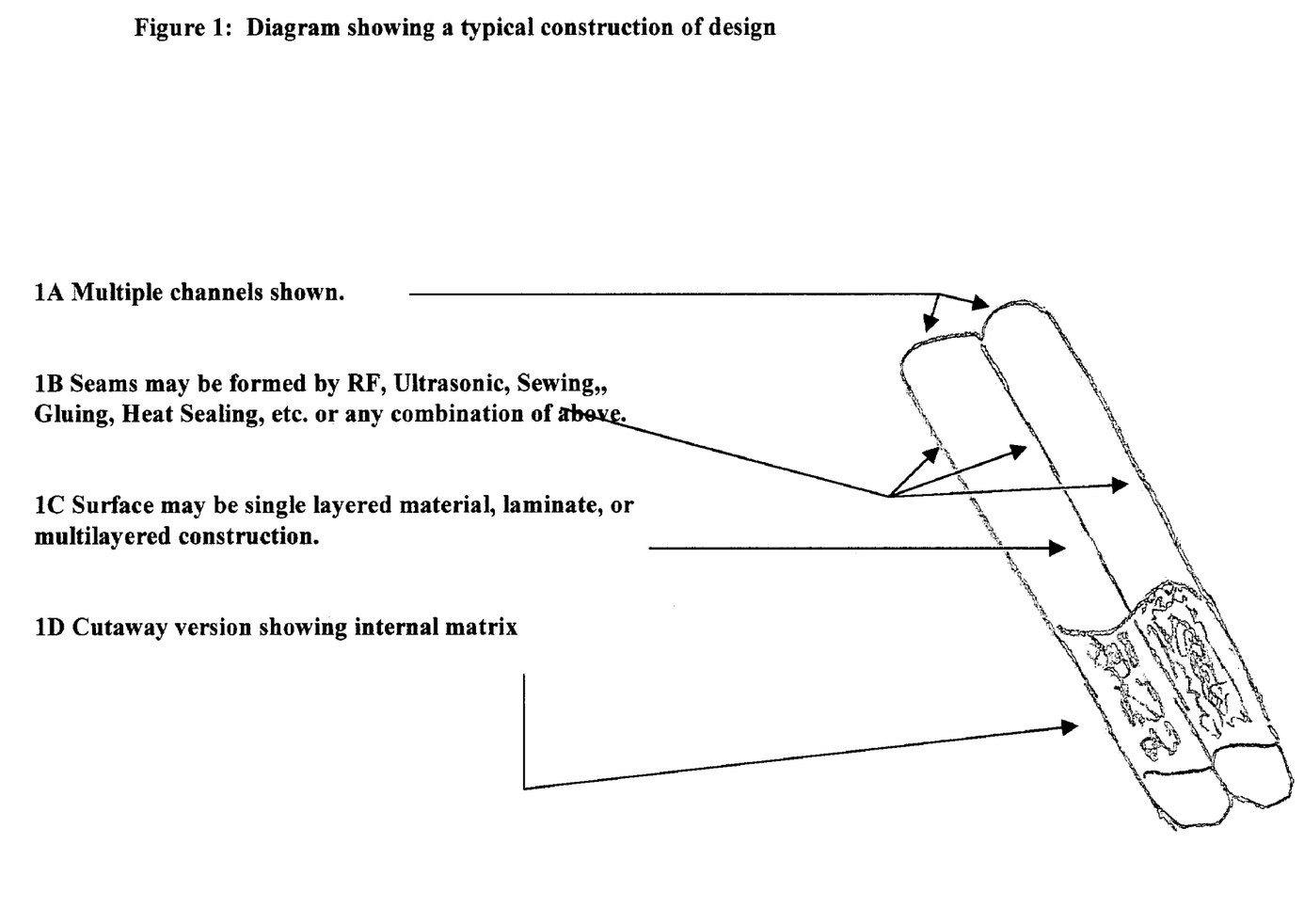
FIG. 1 is a frontal view of one embodiment of the present invention

FIG. 1

FIG. 1 shows a diagram of one embodiment of the invention. 1A illustrates multiple channel construction. 1B shows formation of the channels by RF, Ultrasonic, Gluing, Bonding, Heat Sealing, etc. 1C shows envelope material. ID shows cutaway of a matrix insert.

Figure 2:
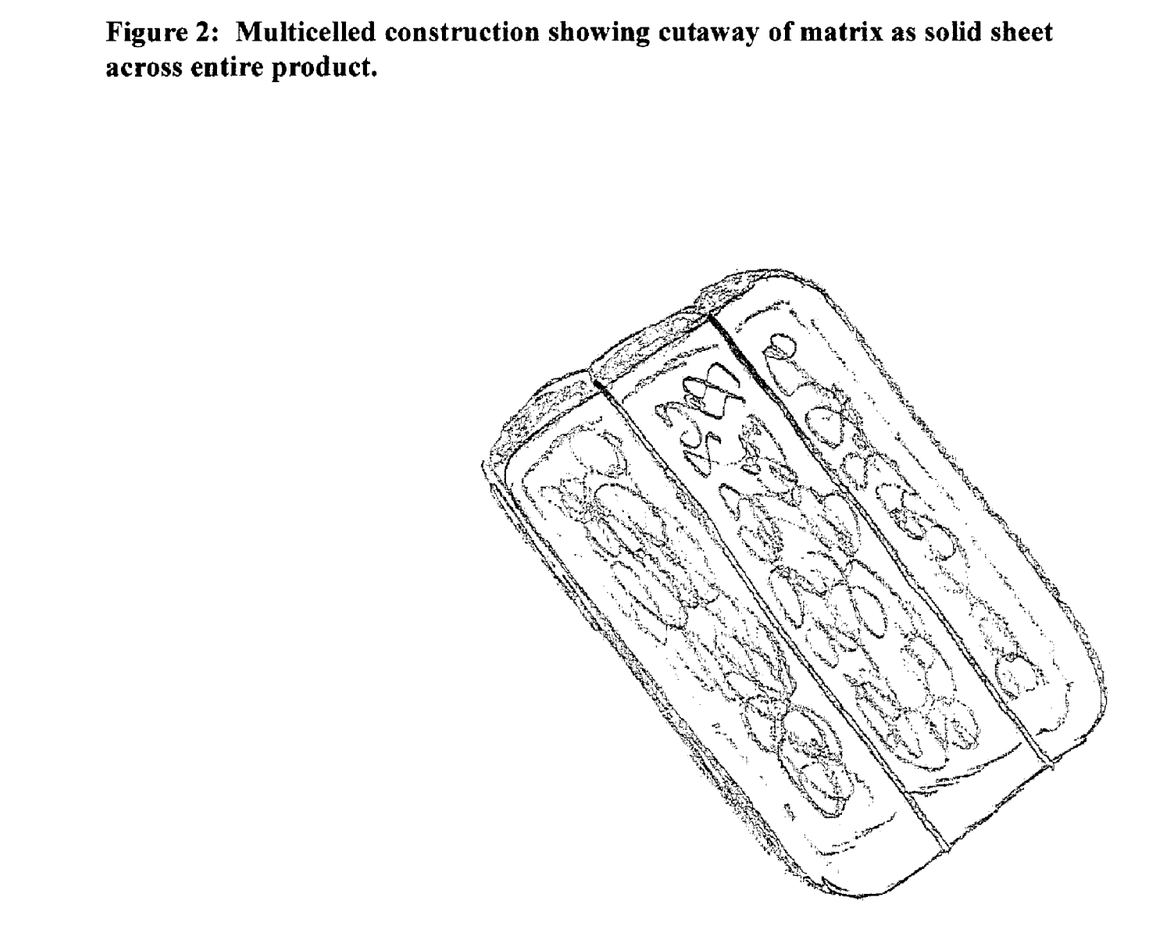
FIG. 2 is a frontal view of another embodiment of the present invention

FIG. 2

FIG. 2 shows a multicelled (multi-channeled) configuration.

Figure 3:
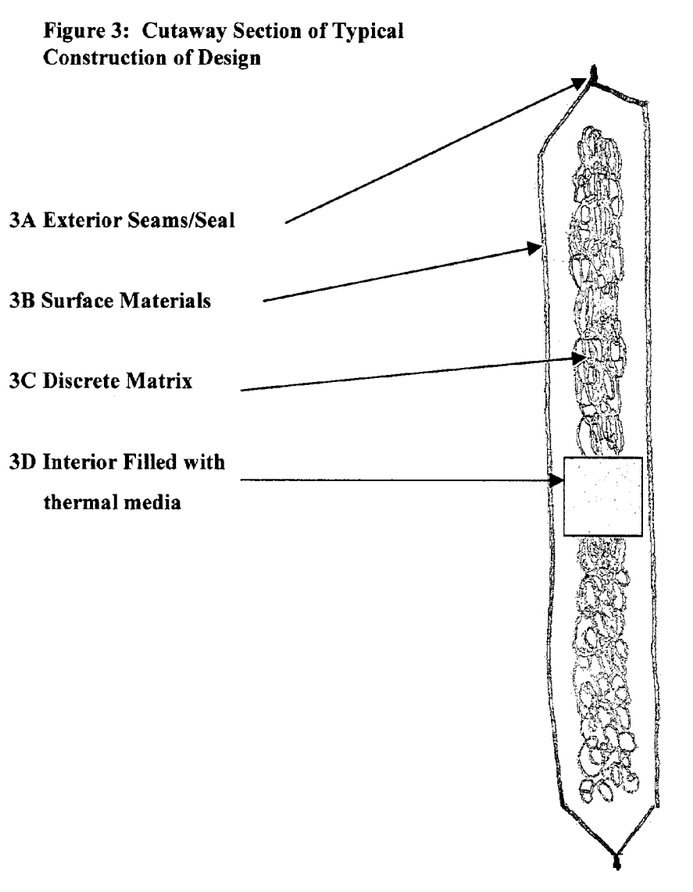
FIG. 3 is a cross-section of the present invention

FIG. 3

FIG. 3 shows a side profile of one embodiment of the invention. 3A indicates an exterior seal used to contain the matrix and thermally conductive fluid, 3B shows envelope construction materials, 3C shows the discrete matrix material, 3D shows the thermal media.

Figure 4:
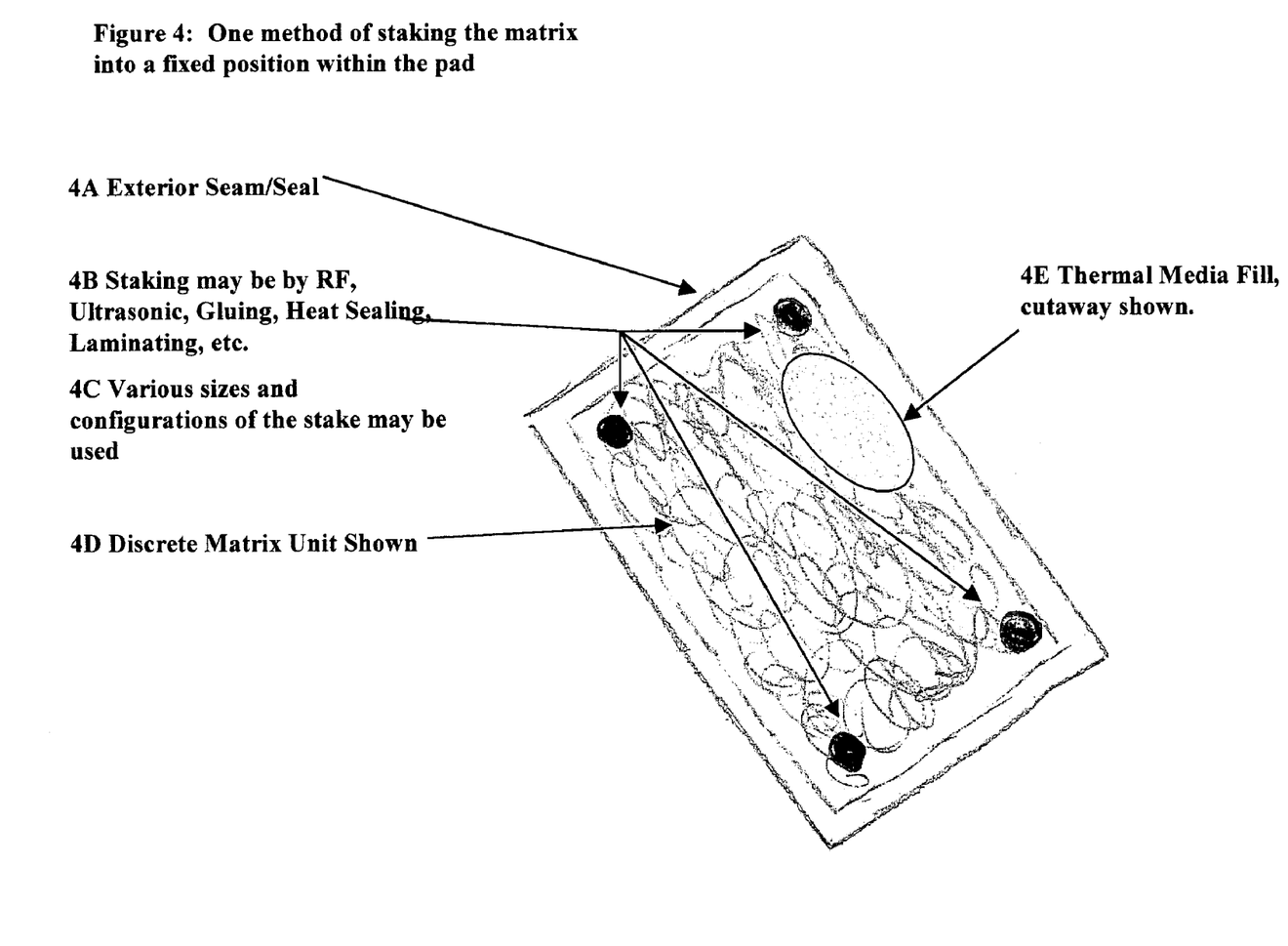
FIG. 4 illustrates one embodiment of the construction details of the present invention

FIG. 4

FIG. 4 illustrates one embodiment of the invention. 4A shows an exterior seam of the envelope. 4B shows staking of the discrete matrix into position at 4 locations along the perimeter. 4D shows a cutaway of the matrix insert.

Figure 5:
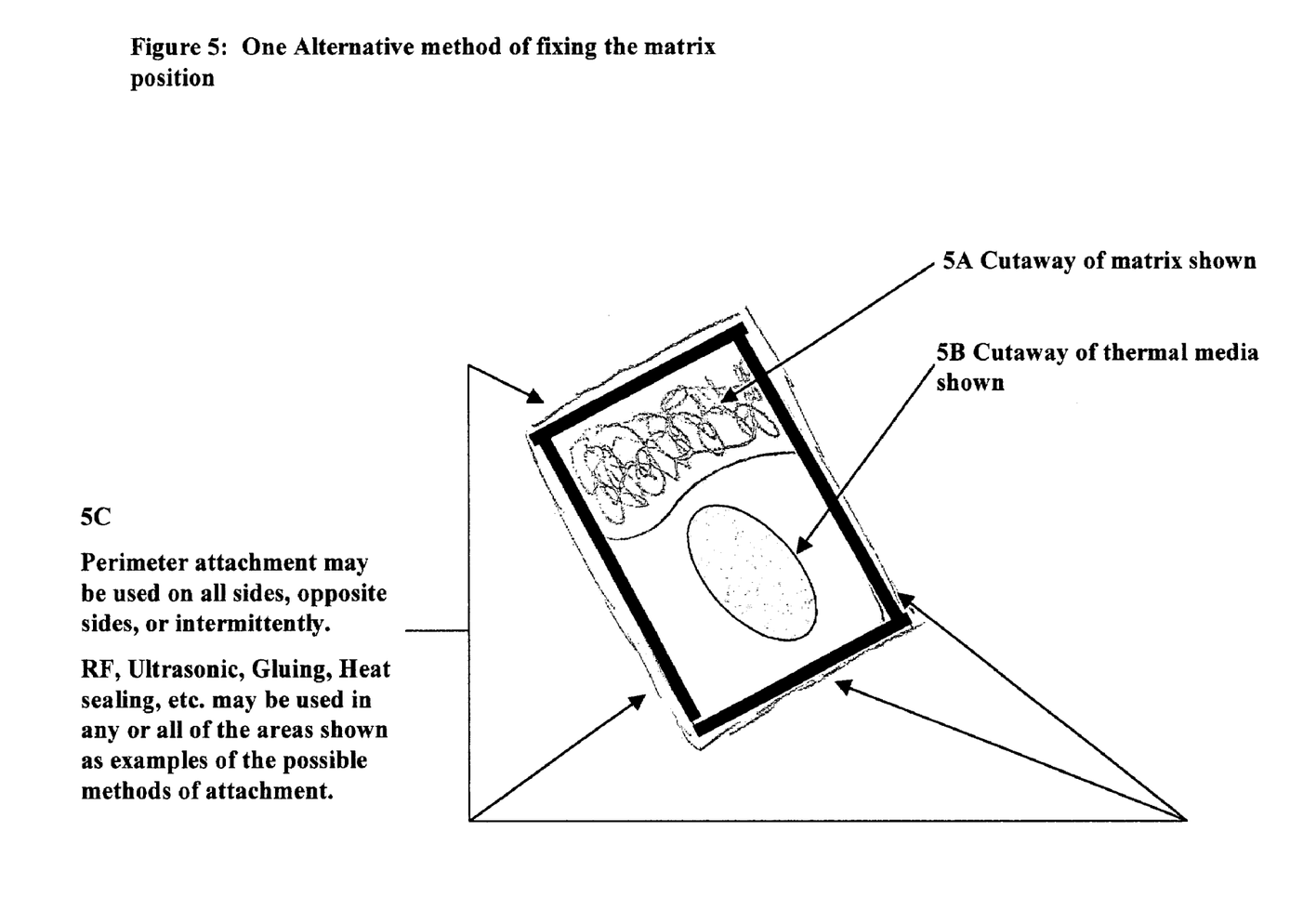
FIG. 5 illustrates another embodiment of the construction details of the present invention

FIG. 5

FIG. 5 illustrates another embodiment of the invention. 5A shows the cut away of the matrix material. 5B is the thermal media. 5C gives a perimeter attachment method.

Figure 6:
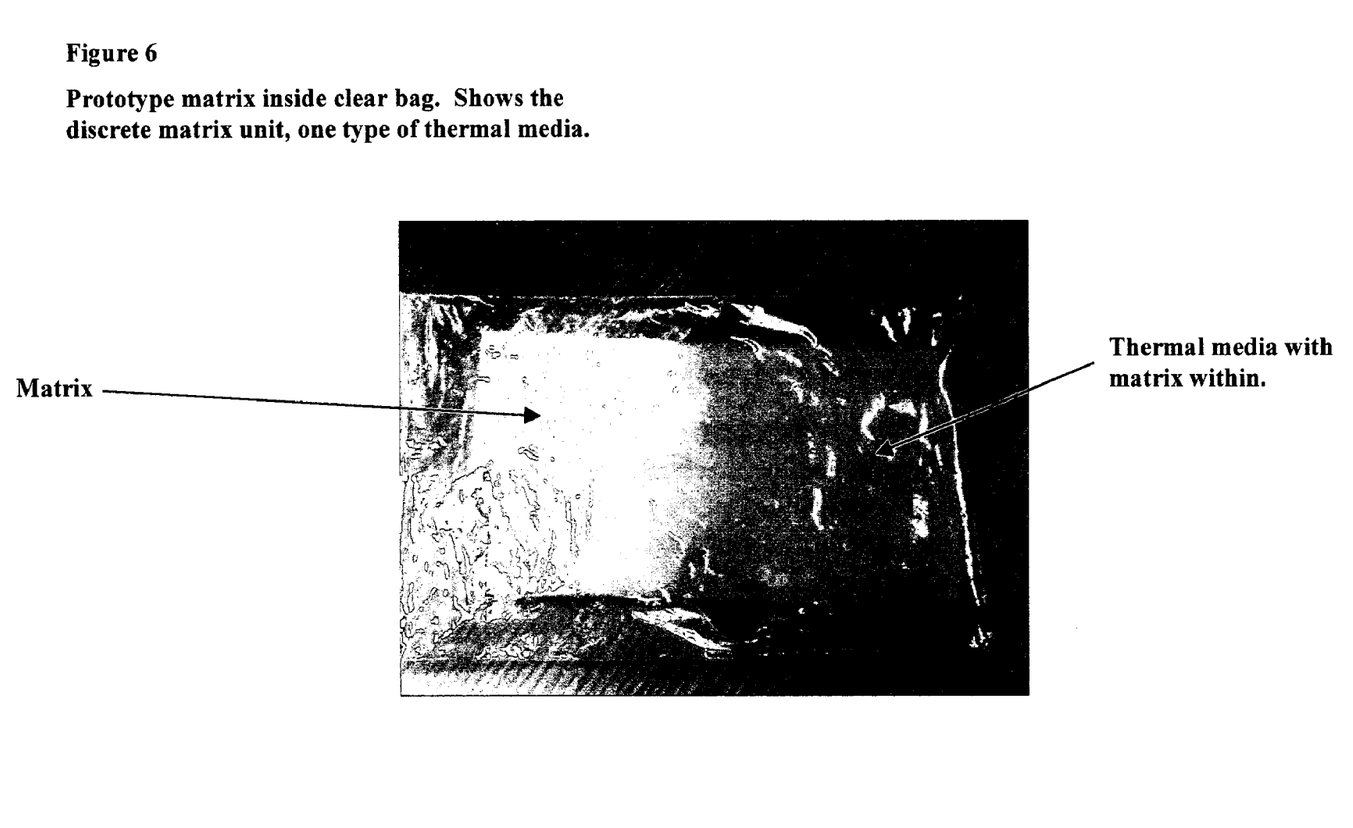
FIGS. 6-9 show various embodiments of construction details of the present invention.
Figure 7:
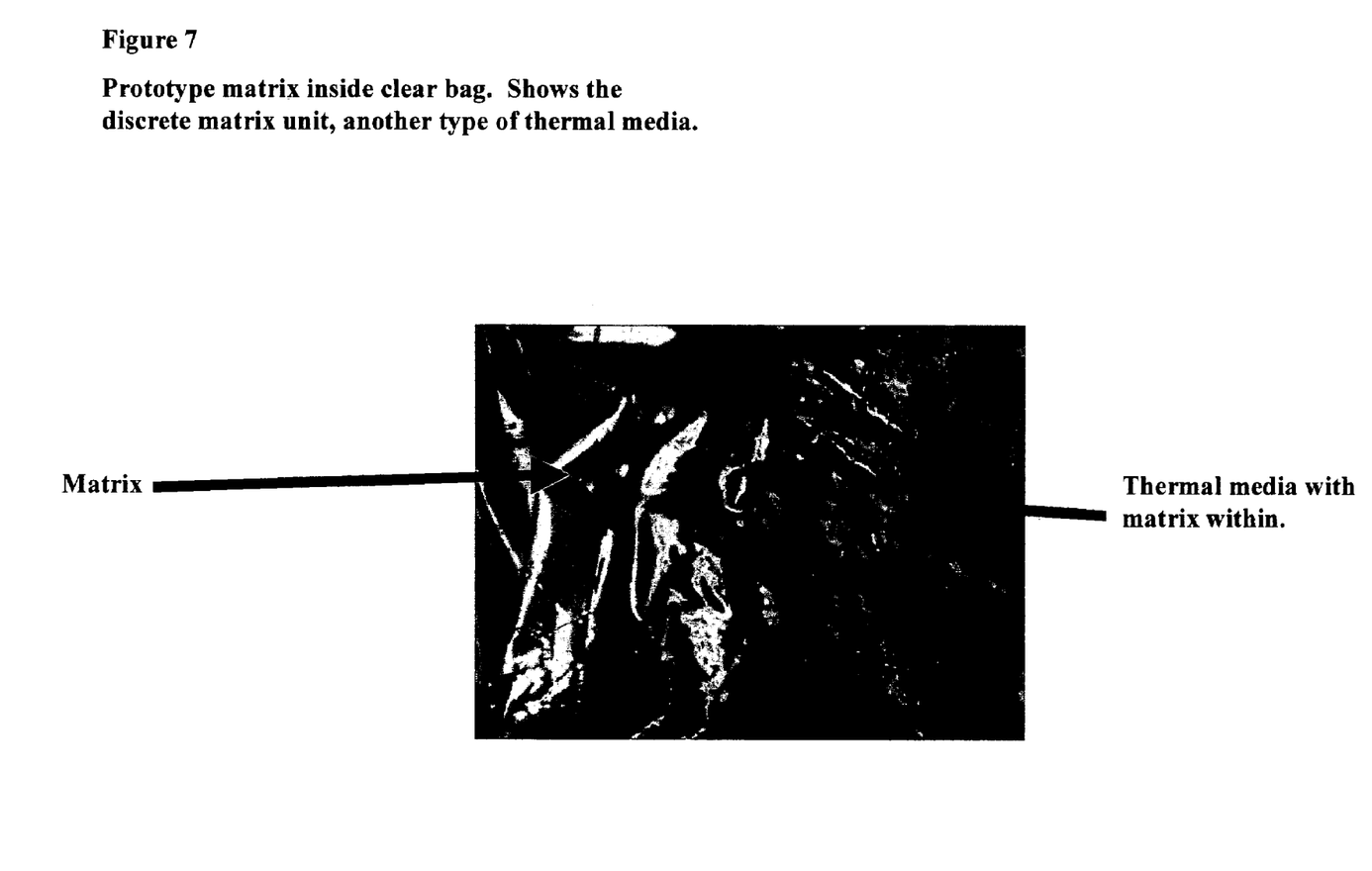

FIG. 6 and FIG. 7

FIGS. 6 and 7 are photographs of a pad showing different thermal media used in conjunction with the matrix. One embodiment of a matrix is shown. Figures show the thermal media present within the matrix, but not fully dispersed in order to illustrate the function of the matrix.

Figure 8:
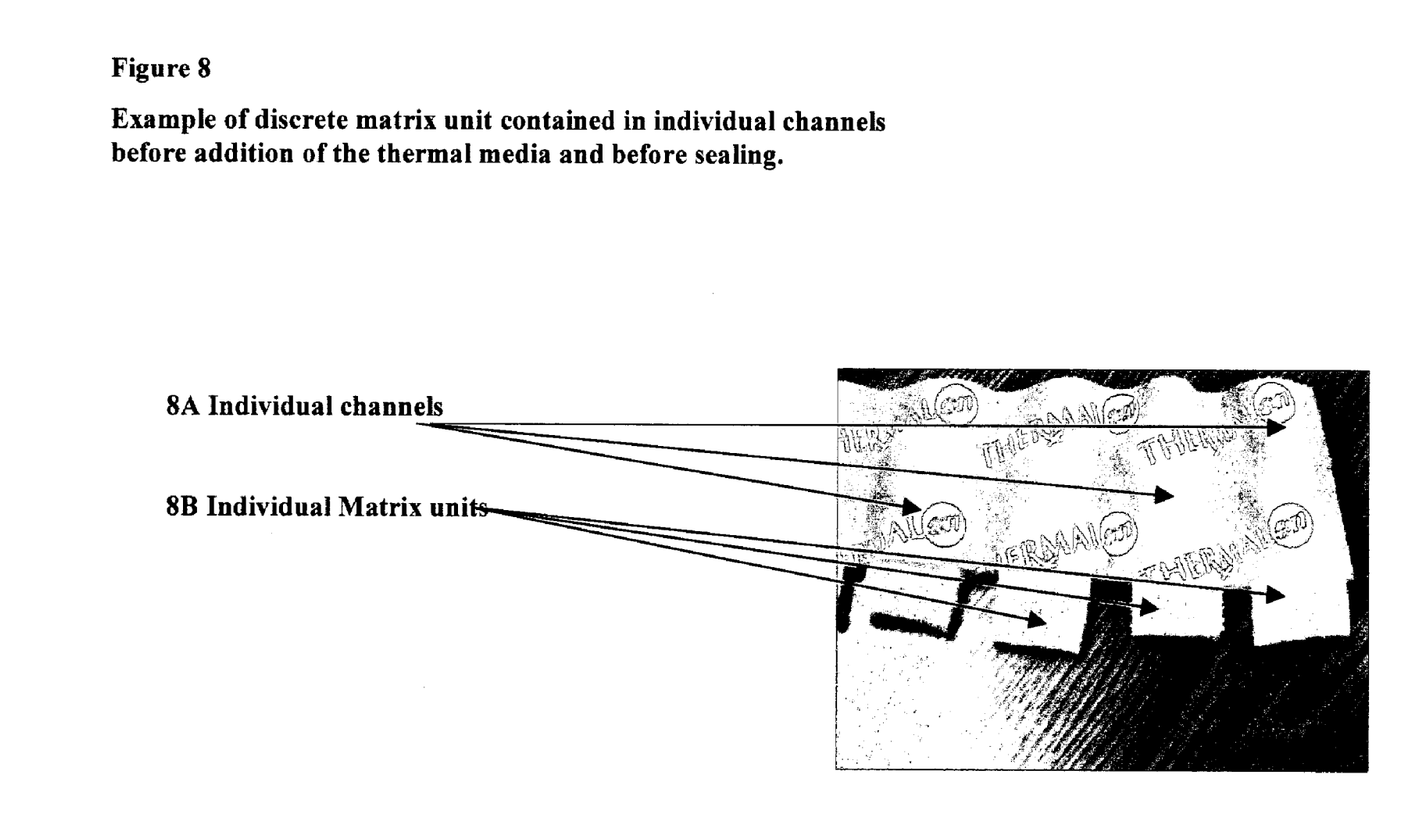

FIG. 8

FIG. 8 shows one construction embodiment with the matrix 8B inserted into individual channels 8B.

Figure 9:
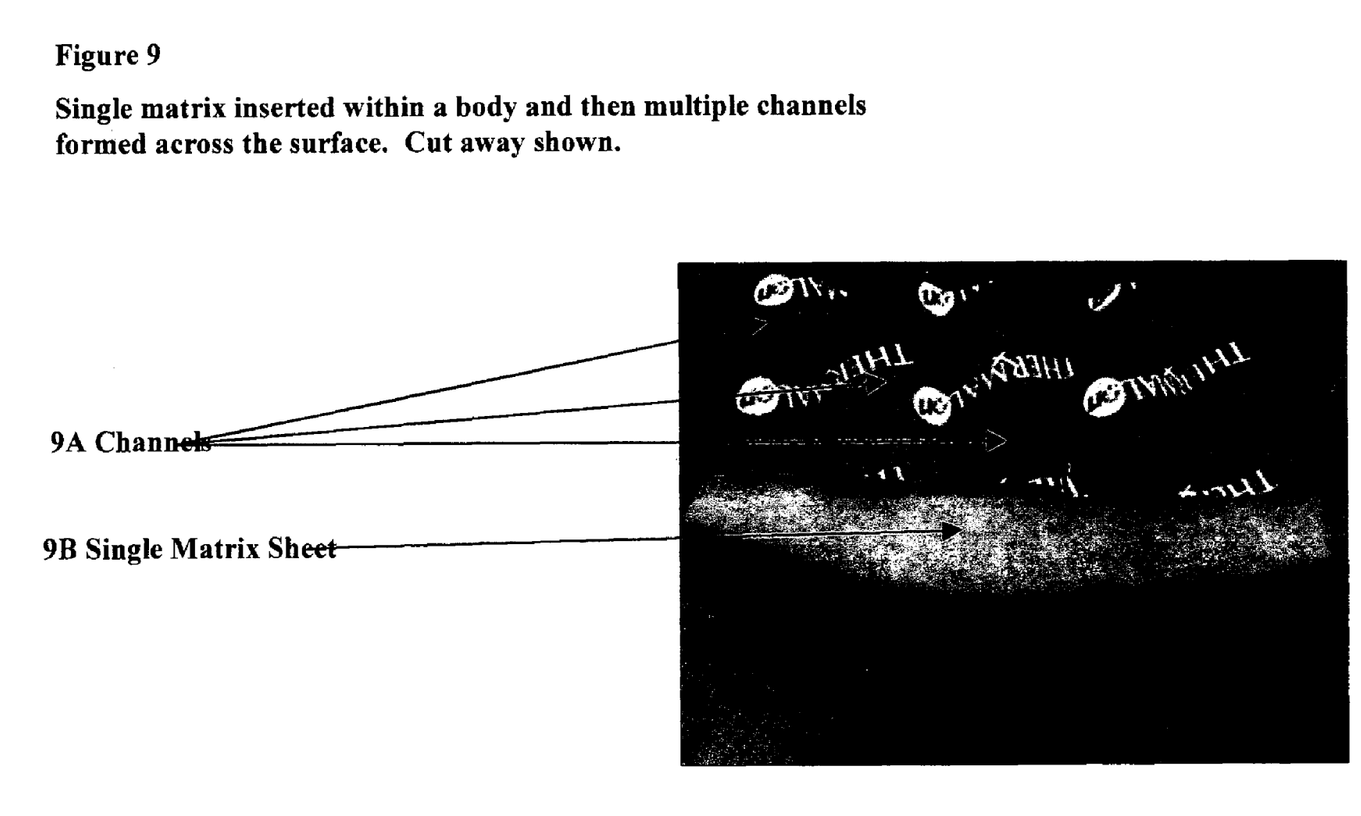

FIG. 9

FIG. 9 shows another construction embodiment with the matrix 9B inserted into an envelope and then having individual channels formed 9B.

Figure 10:
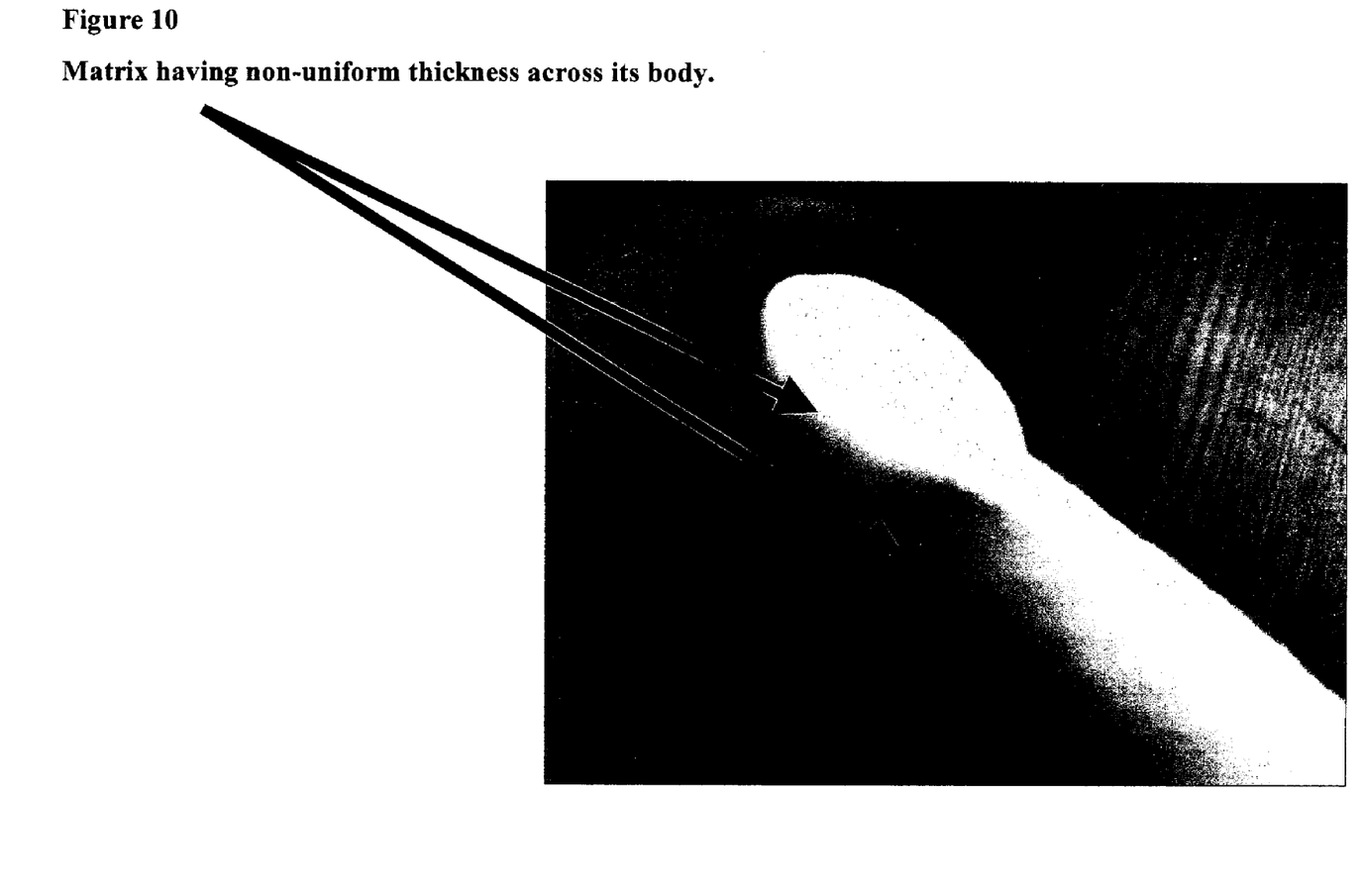
FIGS. 10-11 show various matrix configurations showing more complex geometric possibilities
Figure 11:
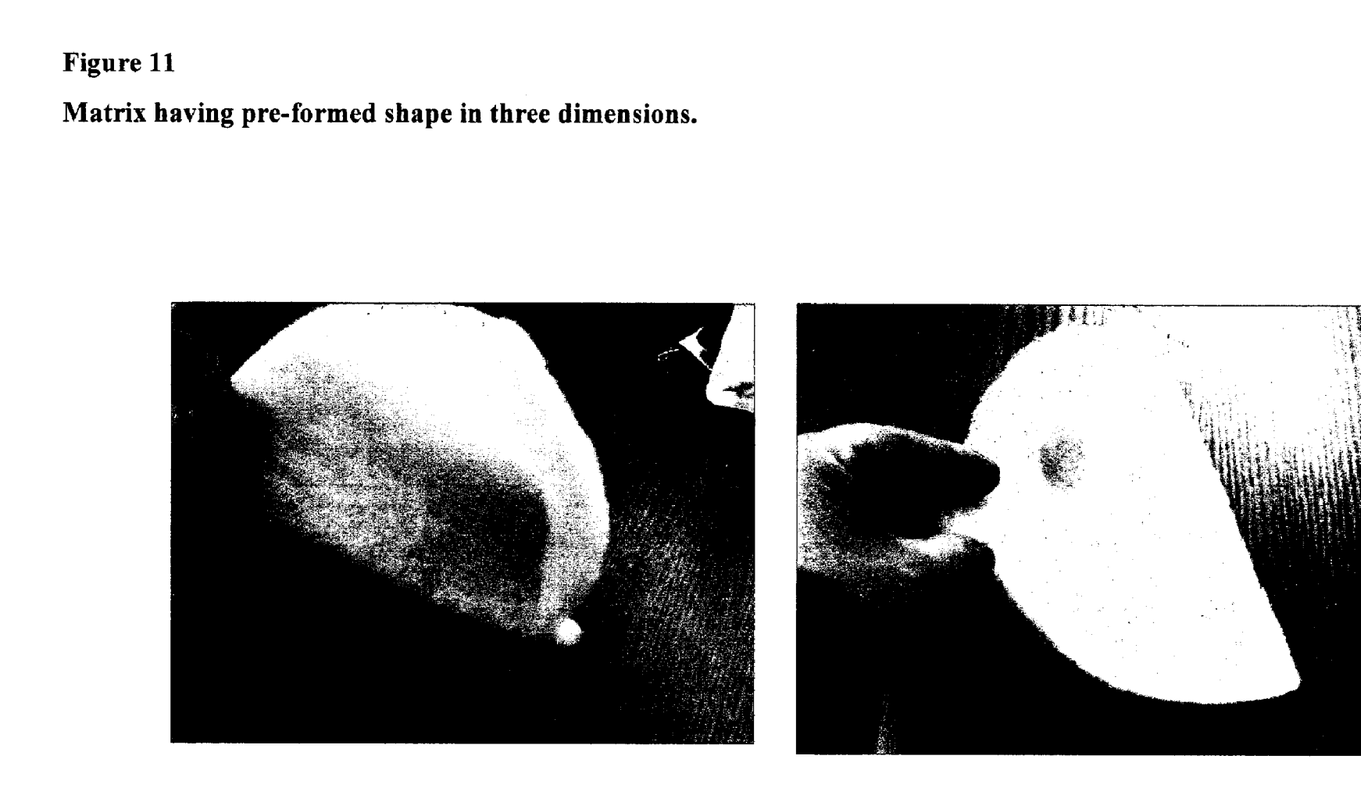

FIG. 10 and FIG. 11

FIGS. 10 and 11 show a matrix construction that is non uniform in shape or thickness. Certain applications lend themselves toward various geometric shapes and orientations. These are examples.

Details of Construction

The invention consists of an outer envelope containing a thermally conductive medium and a discrete matrix insert.

Outer Envelope

The outer envelope serves to contain the thermal media and the matrix. Construction may include, but is not limited to, PVC, polypropylene, polyethylene, polyurethane, silicones, coated woven, knitted, or non-woven textiles, latex materials, laminates, extruded polymers, and various other materials suitable to contain media. Envelope construction may contain various insulation materials or may include construction details to enhance thermal transfer from the pack to the site of application and visa versa. Envelope may utilize sewing, gluing, stitching, ultrasonics, or RF sealing to form the seals, but is not limited to those technologies.

Thermal Media

Various materials are suitable for use as a thermal medium. The key requirements are relatively high heat capacity (0.4 to 1.0) and wide range of operating temperatures (from −20 F. to 230 F. or −50 F to 300 F, for example) with minimal phase change. Low vapor pressure is an added benefit, but not a requirement. Examples may include, but are not limited to, glycerin, propylene glycol, ethylene glycol, and water. Various thickening agents are added to form gels or increase the viscosity of the thermal media. Thickening agents are well known in the industry and may include, but are not limited to, methyl cellulose, PVA, silicates, clays, and bentonite for example. The viscosity of the thickening agents can be equal to or greater than 50 000 cp or 150 000 cp. Additionally, the viscosity of the thickening agents can be less than these values. One embodiment is a 50/50 w/w mixture of glycerin water combined with zeolite to form a 60% by weight clay formulation that is quite viscous.

Matrix

The matrix is a discrete material insert chosen to restrict the movement of the thermal media without chemically bonding to it. Matrix is relatively inert and non-reactive. It does not readily break down, so paper derivatives (cellulosics) are generally unacceptable. Preferred matrix construction is an open, low density, non-woven structure. Matrix may consist of bonded fibers or strands that are randomly assembled to create an open mat that can receive thermal media with minimal entrapment of gas. Air filtration media is one example of material suitable for matrix, as are certain types of non-woven batting materials. Polyester is one preferred embodiment, but other polymeric materials are suitable. Matrix may be attached to the envelope to prevent movement, but it is not essential to product performance. Matrix may consist of bonded fibers or strands that are randomly assembled or bonded together to create an open mat with void space in excess of 50% that can receive thermal media with minimal entrapment of gas. One preferred embodiment of matrix is a melt spun bonded polyester with density of 0.5 pound per cubic foot.

Examples of Use

The invention can be used to deliver a variety of therapeutic modalities. Examples of use include, but are not limited to, the following:

1) Application of heat and/or cold therapy to joints of the hands and feet as found in certain arthritic conditions
2) Application of heat therapy, cold therapy and compression therapy as related to (repetitive stress) injury 3) Simultaneous application of heat therapy and exercise therapy for arthritic fingers
4) Application of contrast therapy to muscle strain of the calf
5) Equestrian heat, cold, and compression therapy to leg quarter
6) Application of heat and cold therapy to hands and/or fingers.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention. The words "a", "an" or "the" can mean one or more, depending upon the context in which the words are used hereinabove.

We claim:

1. An article for use as a pad to deliver therapeutic modality, said article comprising:
   a thermally conductive fluid;
   a discrete matrix insert; and
   an outer envelope sealed to contain the fluid and insert,
   wherein the discrete matrix insert contains fibers bonded together to create a structure with void space in excess of 50%.

2. The article of claim 1, wherein the discrete matrix insert is attached to the envelope.

3. The article of claim 1, wherein the discrete matrix insert is not be attached to the envelope.

4. The article of claim 1, wherein the discrete matrix insert is polymeric and open structured.

5. The article of claim 1, wherein the discrete matrix insert restricts the free flow of the thermally conductive fluid contained within the envelope.

6. The article of claim 1, wherein the discrete matrix insert functions to maintain the relative position of the thermally conductive fluid contained within the envelope.

7. The article of claim 1, wherein the discrete matrix insert is relatively inert with respect to the thermally conductive fluid.

8. The article of claim 1, wherein the envelope functions to retain the contents and is relatively impervious to liquids.

9. The article of claim 1, wherein the envelope is a polymeric material.

10. The article of claim 1, wherein the envelope is a coated (laminated) material.

11. The article of claim 1, wherein the envelope is sealed using heat.

12. The article of claim 1, wherein the envelope is sealed using ultrasonic bonding.

13. The article of claim 1, wherein the envelope is sealed using radio frequency sealing.

14. The article of claim 1, wherein the envelope comprises multiple chambers.

15. The article of claim 1, wherein the thermally conductive fluid has a higher viscosity than water.

16. The article of claim 1, wherein the thermally conductive fluid has a higher viscosity than 50,000 cp.

17. The article of claim 1, wherein the thermally conductive fluid has a viscosity higher than 150,000 cp.

18. The article of claim 1, wherein the thermally conductive fluid has a heat capacity greater than 0.4.

19. The article of claim 1, wherein the thermally conductive fluid is stable over a wide range of operating temperatures (−10 F. to 250 F.).

20. The article of claim 1, wherein the thermally conductive fluid is stable over a wide range of operating temperatures (−50 F. to 300 F.).

21. The article of claim 1, wherein the thermally conductive fluid has a vapor pressure less than pure water.

22. The article of claim 1, wherein the therapeutic modality is heat.

23. The article of claim 1, wherein the therapeutic modality is cold.

24. An article for use as a sad to deliver thera eutic modality, said article comprising:
   a the mall conductive fluid;
   a discrete matrix insert; and
   an outer envelope sealed to contain the fluid and insert,
   wherein the discrete matrix insert comprises multiple layers positioned successively on top of each other.

25. The article of claim 24, wherein the layers are physically joined.

26. An article for use as a pad to deliver therapeutic modality, said article comprising:
   a thermally conductive fluid;
   a discrete matrix insert; and
   an outer envelope sealed to contain the fluid and insert,
   wherein the discrete matrix insert comprises multiple layers of material of differing physical characteristics.

27. The article of claim 26, wherein the layers are be physically joined.

* * * * *